United States Patent [19]

Schlager

[11] 4,261,987

[45] Apr. 14, 1981

[54] 3-DI-N-PROPYL-ACETOXY-BENZODIAZE-PINE-2-ONES AND PHARMACEUTICAL COMPOSITIONS THEREOF

[75] Inventor: Ludwig H. Schlager, Vienna, Austria

[73] Assignee: Gerot Pharmazeutika Gesellschaft m.b.H., Vienna, Austria

[21] Appl. No.: 970,057

[22] Filed: Dec. 14, 1978

[30] Foreign Application Priority Data

Dec. 14, 1977 [AT] Austria .................................. 8938/77
Nov. 21, 1978 [AT] Austria .................................. 8312/78

[51] Int. Cl.$^3$ .................... C07D 243/24; A61K 31/55
[52] U.S. Cl. ............................. 424/244; 260/239.3 D
[58] Field of Search .................. 260/239.3 D; 424/244

[56] References Cited

U.S. PATENT DOCUMENTS

| | | | |
|---|---|---|---|
| 3,176,009 | 3/1965 | Bell ................................ | 260/239.3 D |
| 3,236,838 | 2/1966 | Archer et al. ................. | 260/239.3 D |
| 3,299,053 | 1/1967 | Archer et al. ................. | 260/239.3 D |
| 3,391,138 | 7/1968 | Archer et al. ................. | 260/239.3 D |
| 3,801,568 | 4/1974 | Nudelman et al. ........... | 260/239.3 D |

FOREIGN PATENT DOCUMENTS

242706 10/1965 Austria .............................. 260/239.3 D
2519318 11/1975 Fed. Rep. of Germany ... 260/239.3 D

OTHER PUBLICATIONS

Chemical Abstracts, vol. 71 (1969), Item 13109h, abstracting De Marchi et al., in "Chim. Thor." (1968), vol. 3, No. 6, pp. 430–432.

Sternbach et al., Some Aspects of Structure–Activity Relationship in Psychotropic Agents of the 1,4-Benzodiazepine Series, *CSTR*, New Delhi, India (1966).

Negwer "Organic-Chemical Drugs and Their Synonyms", Akademie-Verlag, Berlin (1978), p. 1242.

Merck Index, 9th Edition, (1976), p. 9576, Merck and Co., Inc., Rahway, New Jersey (1976).

*Primary Examiner*—Robert T. Bond
*Attorney, Agent, or Firm*—Sughrue, Rothwell, Mion, Zinn and Macpeak

[57] ABSTRACT

Novel 3-Di-n-Propyl-Acetoxy-Benzodiazepine-2-Ones and use thereof as anti-convulsant compounds.

4 Claims, No Drawings

3-DI-N-PROPYL-ACETOXY-BENZODIAZEPINE-2-ONES AND PHARMACEUTICAL COMPOSITIONS THEREOF

The invention relates first of all to new 3-di-n-propyl-acetoxy-benzodiazepine-2-ones of the general formula

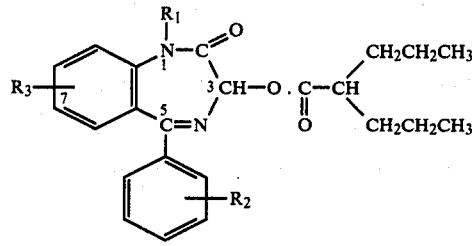

wherein $R_1$ represents hydrogen, a low alkyl radical, alkoxy alkyl radical, acyloxy alkyl radical, dialkyl aminoalkyl radical or N,N-dialkyl-carbamyl alkyl radical and $R_2$ as well as $R_3$ may signify hydrogen, halogen, trifluoromethyl or nitro, with the condition that $R_1$ and $R_2$ do not signify hydrogen simultaneously, whenever $R_3$ is a chlorine atom in position 7.

The invention relates especially to 7-chloro-3-dipropylacetoxy-5-(2′-fluorophenyl)-1,3-dihydro-2H-1,4-benzodiazepine-2-one, 7-chloro-3-dipropylacetoxy-5-(2′-chlorophenyl)-1,3-dihydro-2H-1,4-benzodiazepine-2-one and 1-methyl-7-chloro-3-dipropylacetoxy-5-phenyl-1,3-dihydro-2H-1,4-benzodiazepine-2-one.

Of the valproic acid esters of the general formula I, only one derivative has been described hitherto in the patent literature: the compound with $R_1=R_2=$hydrogen and $R_3=$7-chlorine is obtained according to the data in Chim. Ther. 3, 430 (1968) by treatment of a cooled suspension of 7-chloro-3-hydroxy-5-phenyl-1,3-dihydro-2H-1,4-benzodiazepine-2-one (Oxazepam) in pyridine with dipropyl acetic acid chloride. This Oxazepam ester of the valproic acid was investigated pharmacologically by F. de Marchi and M. V. Torrielli (l.c.) concerning its anticonvulsive effect as compared to Metrazol (Pentetrazol). In the case of intraperitoneal application, the Italian authors found a DE 50 of 163 mg/kg for the valproic acid and for the corresponding Oxazepam ester, such of 360 mg/kg. The ester accordingly and in order to achieve an equal effect, would have to be dosed more than twice as high as the valproic acid itself, the individual dose of which already lies relatively high anyway in medications at about 300 mg. This unfavorable finding apparently led to the fact that no group of researchers would deal any more with other valproic acid esters of 3-hydroxy-benzodiazepine-2-ones.

Suprisingly, it was now found that some valproic acid esters of the general formula I in the case of oral administration in the Metrazol test are more than 100 times superior to valproic acid and the anticonvulsive effect of such esters lasts a particularly long time (Table 1). Moreover, in the case of the esters according to the invention and in view of the benzodiazepine component, an advantageously modified action profile is recognizable.

TABLE 1

| Anticonvulsive test substance | METRAZOL TEST: DE 50 (mg/kg) | | | |
| --- | --- | --- | --- | --- |
| | Values by Gerot (mouse, oral) | | N.I.H. values (mouse, s.c.) | |
| Ester of the general formula I from Example No. | duration of the experiment in hours: | | | |
| | 0.5 | 2 | 6 | 4 |
| 1 | 2.97 | ~1.0 | <1.0 | 1.1 |
| 2 | 2.21 | <1.0 | ~2.0 | 2.35 |
| Valproic acid | 350 | 487 | — | — |

As becomes clear from Table 1, the ester obtainable according to Example 1 acts in the Metrazol test after 2 hours 487 times as strongly as valproic acid. At the same time the "Gerot values" obtained in the case of oral application are well in agreement with the "N.I.H. values" found in the case of subcutaneous injection. The latter were found within the scope of the "Anticonvulsant Screening Project" in the National Institute of Health, Bethesda.

Correspondingly, the present invention also relates to spasmolytically active medicaments, which contain a compound of the general formula I as an active substance. Spasmolytics, which contain 7-chloro-3-dipropylacetoxy-5-(2′-fluorophenyl)-1,3-dihydro-2H-1,4-benzodiazepine-2-one, 7-chloro-3-dipropylacetoxy-5-(2′-chlorophenyl)-1,3-dihydro-2H-1,4-benzodiazepine-2-one or 1-methyl-7-chloro-3-dipropylacetoxy-5-phenyl-1,3-dihydro-2H-1,4-benzodiazepine-2-one as an active component are especially suitable.

The acute toxicity of the compounds according to the invention is extraordinarily low; thus, f. ex., the LD 50 of the compound obtainable according to Example 1, lies higher than 5000 mg/kg (mouse, oral).

Finally, the present invention also refers to the production of the compounds according to the invention. These new compounds may be produced by reacting a 3-hydroxy-1,4-benzodiazepine of the general formula

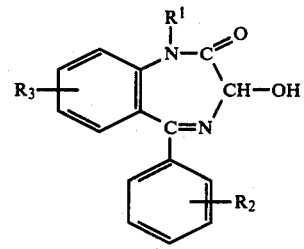

in which the radicals $R_1$, $R_2$ and $R_3$ have the above meaning, preferably in a solvent or in a solvent mixture with a compound of the general formula

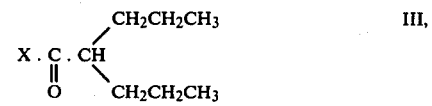

wherein X represents a radical separable while forming HX, f. ex., halogen, OH or the di-n-propyl-acetoxy radical, and this conversion is accomplished preferably in the presence of one or several HX-binding agents.

The starting products of the general formula II are accessible in a known manner (f. ex., according to Austrian Pat. No. 309,436, or Arzneim.-Forsch. 25, 720 (1975). New derivatives of the general formula II are easily obtainable according to this known process; thus, f. ex., the derivative with $R_1$=N,N-diethylcarbamyl-methyl, $R_2$=hydrogen and $R_3$=7-chlorine by conversion of Oxazepam with sodium hydride and subsequently with chloroacetic acid diethyl amide in 1,2-dimethoxyethane. The reaction product forms colorless crystals from methanol which at 215° C. show a crystal change over and decompose at 223°–233° C. Further, new compounds of the formula II have been summarized in Table 2.

TABLE 2
New Compounds of the Formula II

| $R_1$ | $R_2$ | $R_3$ | Melting point °C. |
|---|---|---|---|
| $C_2CH_2O . COCH_3$ | H | 7-Cl | 161–163 |
| $CH_2CH_2O . COCH_3$ | 2'-Cl | 7-Cl | 189–191 |
| $CH_2CH_2O . COCH_3$ | 2'-F | 7-Cl | 173–178 |

The reaction partners of the general formula III are producible in accordance with processes described in the literature.

Several processes have already been known for the synthesis of 3-acyloxy-benzodiazepine-2-ones: especially the Polonovsky rearrangement of benzodiazepine-2-one-4-oxides with acylating agents (Austrian Pat. No. 242,706; German Pat. No. 2,237,211), furthermore, the similar reaction of open chain N-oxides with acid anhydrides (Austrian Pat. No. 256,113) or the conversion of 3-halogen-benzodiazepine-2-ones with acyloxy components (Austrian Pat. Nos. 266,146, 267,531).

Although from the 3-acyloxy-benzodiazepine-2-ones, accessible by these processes, pharmacological effects have been stated, the 3-acyloxy derivatives—as becomes clear from the Austrian Pat. No. 256,113—preferably serve as intermediate products for obtaining the therapeutically used 3-hydroxy compounds. It is therefore understandable that the reverse way, namely the synthesis of 3-acyloxy-benzodiazepine-2-ones from the 3-hydroxy compounds is hardly practiced. Insofar as such 3-acyloxy derivatives do appear at all in lists of medicaments, we are dealing however with succinates and pivalates which are active as psychosedatives and tranquilizers (M. Negwer: "Organic-chemical Medicaments and their synonyms", 5th Edition, 1978, No. 3843, 6497, 6498).

The production of the new esters of the general formula I may thus take place either according to the known process by conversion of a compound of the general formula II with dipropyl acetic acid chloride in pyridine or advantageously, f. ex. with dipropyl acetic acid anhydride in an aprotic solvent in the presence of a tertiary amine. Beyond that, other variations of the process customary for the production of esters may also be used, in so far that they do not require (in the case of compounds with $R_1$=H) a heating in the acid medium, since under these conditions, the diazepine ring of II (with $R_1$=H) narrows down to the quinazoline ring according to experience (J. Org. Chem. 29, 506–507 (1964).

Furthermore, the compounds according to the invention may also be produced by reacting a benzodiazepine-2-one-4-oxide of the general formula

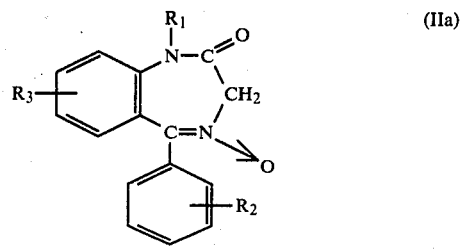

(IIa)

in which the radicals $R_1$, $R_2$ and $R_3$ have the above meaning, preferably in an inert solvent or solvent mixture and, if desired, in the presence of a tertiary amine with the compound of the general formula

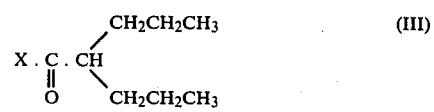

(III)

in which X represents halogen or the di-n-propyl-acetoxy radical.

The starting products of the general formula IIa are accessible in a known manner (f. ex., according to Austrian Pat. Nos. 308,753; 223,620, J. Org. Chem. 27. 562 (1962), Arzneim.-Forsch. 25, 720 (1975), German OS No. 2,237,211). New derivatives of the general formula IIa may easily be obtained according to this known process.

The reaction partners of the general formula III may be produced according to processes described in literature.

The production of the new esters of the general formula I may thus also take place in accordance with the process of the so-called Polonovsky rearrangement known per se by conversion of a compound of the general formula IIa, f. ex., with dipropyl acetic acid chloride or dipropyl acetic acid anhydride in an inert solvent and, if desired, also in the presence of a tertiary amine.

By the following examples, the invention is to be explained in more detail but not be limited to them.

EXAMPLE 1

A suspension of 13.4 g of 7-chloro-3-hydroxy-5-(2'-fluorophenyl)-1,3-dihydro-2H-1,4-benzodiazepine-2-one (melting point: 195°–198°) in 35 ml absolute pyridine is mixed under exclusion of atmospheric humidity at 0° while stirring drop by drop with 7.3 g of dipropyl acetic acid chloride. It is agitated for one hour at 0° and for 5 hours at ambient temperature, and the mixture is allowed to stand over night. The oil developing by pouring in ice water is separated by decanting and crystallized while mixing with ethanol by stirring. After the recrystallization from acetonitrile/water, the colorless 7-chloro-3-dipropyl acetoxy-5-(2'-fluoro-phenyl)-1,3-dihydro-2H-1,4-benzodiazepine-2-one obtained, melts at 147°–149°.

EXAMPLE 2

While stirring, 28 g of dipropyl acetic acid anhydride are added drop by drop to a mixture of 16.7 g of 7-chloro-3-hydroxy-5-(2'-chloro-phenyl)-1,3-dihydro-2H-1,4-benzodiazepine-2-one (Lorazepam) and 6.3 g of triethylamine in 50 ml of absolute 1,2-dimethyloxyethane, and this is heated to 50° excluding atmospheric moisture. After 15 hours, the solution treated with activated charcoal and filtered is evaporated in the vacuum, the residue is absorbed in chloroform and extracted twice with water. The chloroform solution dried by way of $Na_2SO_4$ is evaporated, the residue crystallizes from isopropyl ether. By recrystallization from acetonitrile, one will obtain the colorless 7-chloro-3-dipropylacetoxy-5-(2'-chlorophenyl)-1,3-dihydro-2H-1,4-benzodiazepine-2-one, which melts at 191°–193°.

EXAMPLE 3

A solution of 15 g of 1-methyl-7-chloro-3-hydroxy-5-phenyl-1,3-dihydro-2H-1,4-benzodiazepine-2-one (Temazepam) and 5 g of absolute pyridine is cooled in 40 ml of freshly distilled dimethyl formamide to −5° and is mixed drop by drop with 10.5 g of dipropyl acetic acid chloride with the exclusion of atmospheric moisture. The mixture is stirred for an additional 4 hours at −5° and is allowed to stand over night at 0°, and then the mixture is poured on ice. The separated oil crystallizes while rubbed on with ethanol. By recrystallization from petroleum ether or isopropanol using activated charcoal, one will obtain the 1-methyl-7-chloro-3-dipropylacetoxy-5-phenyl-1,3-dihydro-2H-1,4-benzodiazepine-2-one as a colorless powder with a melting point of 134°–136°.

EXAMPLE 4

A suspension of 10 g of 7-chloro-5-(2'-fluoro-phenyl)-1,3-dihydro-2H-1,4-benzodiazepine-2-one-4-oxide in 20 ml of absolute chloroform is mixed with 14.3 g of dipropyl acetic acid anhydride and is heated under reflux and with the exclusion of atmospheric moisture for such a length of time until a sample on the thin layer-chromatogram (silica gel 60 F 254 of the firm Merck, flow agent: cyclohexane/acetone=1:1) shows a complete conversion. Then, the cooled mixture is shaken out several times with water, the organic phase is dried with $Na_2SO_4$ and the filtrate is evaporated in the vacuum. Upon standing over night, the residue crystallizes, is washed with petroleum ether and recrystallized from aceontrile. One will obtain a colorless powder of 7-chloro-3-dipropylacetoxy-5-(2'-fluorophenyl)-1,3-dihydro-2H-1,4-benzodiazepine-2-one, which melts at 147°–149°.

EXAMPLE 5

According to the process of Example 4, one will obtain the new 7-chloro-3-dipropylacetoxy-5-(2'-chlorophenyl)-1,3-dihydro-2H-1,4-benzodiazepine-2-one, which melts at 191°–193°, from 7-chloro-5-(2'-chlorophenyl)-1,3-dihydro-2H-1,4-benzodiazepine-2-one-4-oxide.

According to the process of the invention, one will also obtain f. ex., the derivatives listed in the following table 3:

TABLE 3

| Derivatives of the formula I | | | |
|---|---|---|---|
| $R_1$ | $R_2$ | $R_3$ | m.p. °C. |
| $CH_3$ | H | 7-Cl | 134–136 |
| $CH_2CH_2N(C_2H_5)_2$ | H | 7-Cl | 140–142 |
| $CH_2CH_2N(C_2H_5)_2$ | 2'-Cl | 7-Cl | 136–138 |
| $CH_2CON(C_2H_5)_2$ | H | 7-Cl | 149–152 |
| $CH_2CH_2O . COCH_3$ | H | 7-Cl | 147–149 |
| $CH_2CH_2O . COCH_3$ | 2'-Cl | 7-Cl | 98–101 |
| $CH_2CH_2O . COCH_3$ | 2'-F | 7-Cl | 112–115 |
| H | H | 7-$NO_2$ | 219–221 |

I claim:
1. 7-Chloro-3-dipropylacetoxy-5-(2'-fluorophenyl)-1,3-dihydro-2H-1,4-benzodiazepine-2-one.
2. 7-Chloro-3-dipropylacetoxy-5-(2'-chlorophenyl)-1,3-dihydro-2H-1,4-benzodiazepine-2-one.
3. An anti-convulsively effective pharmaceutical composition comprising an anti-convulsively effective amount of the compound of claim 1 and a pharmaceutically acceptable carrier.
4. An anti-convulsively effective pharmaceutical composition comprising an anti-convulsively effective amount of the compound of claim 2 and a pharmaceutically acceptable carrier.

* * * * *